United States Patent [19]
Funderburk et al.

[11] Patent Number: 5,545,152
[45] Date of Patent: Aug. 13, 1996

[54] QUICK-CONNECT COUPLING FOR A MEDICATION INFUSION SYSTEM

[75] Inventors: Jeffery V. Funderburk, Granada Hills; Deborah C. McIntyre, Agoura Hills, both of Calif.

[73] Assignee: MiniMed Inc., Sylmar, Calif.

[21] Appl. No.: 328,782

[22] Filed: Oct. 28, 1994

[51] Int. Cl.$^6$ .................................................. A61M 25/00
[52] U.S. Cl. ............................................. 604/283; 604/905
[58] Field of Search ..................................... 604/283, 905, 604/86, 88, 411–415, 242, 243, 240, 131

[56] References Cited

U.S. PATENT DOCUMENTS

| | | |
|---|---|---|
| 3,512,524 | 5/1970 | Drewe . |
| 3,986,508 | 10/1976 | Barrington . |
| 4,294,249 | 10/1981 | Sheehan et al. . |
| 4,508,367 | 4/1985 | Oreopoulos et al. . |
| 4,511,359 | 6/1985 | Vaillancourt . |
| 4,752,292 | 6/1988 | Lopez et al. . |
| 4,755,173 | 7/1988 | Konopka et al. . |
| 4,946,445 | 8/1990 | Lynn . |
| 4,950,260 | 8/1990 | Bonaldo . |
| 4,964,855 | 10/1990 | Todd et al. . |
| 4,981,469 | 1/1991 | Whitehouse et al. . |
| 4,998,713 | 3/1991 | Vaillancourt . |
| 4,998,925 | 3/1991 | Al-Sioufi et al. . |
| 5,067,950 | 11/1991 | Broadnax, Jr. . |
| 5,088,984 | 2/1992 | Fields . |
| 5,120,324 | 6/1992 | Sancoff . |
| 5,122,123 | 6/1992 | Vaillancourt . |
| 5,122,129 | 6/1992 | Olson et al. . |
| 5,139,485 | 8/1992 | Ryan . |
| 5,171,214 | 12/1992 | Kolber et al. . |
| 5,176,662 | 1/1993 | Bartholomew et al. . |
| 5,199,947 | 4/1993 | Lopez et al. . |
| 5,201,717 | 4/1993 | Wyatt et al. . |
| 5,281,206 | 1/1994 | Lopez . |
| 5,292,308 | 3/1994 | Ryan . |

FOREIGN PATENT DOCUMENTS

| | | | |
|---|---|---|---|
| 0063333 | 10/1982 | European Pat. Off. | ............. 604/905 |
| 0615768A2 | 1/1994 | European Pat. Off. . | |
| WO94/22520 | 10/1994 | WIPO . | |

*Primary Examiner*—John D. Yasko
*Attorney, Agent, or Firm*—Kelly Bauersfeld & Lowry

[57] ABSTRACT

A quick-connect coupling is provided for use in a medication infusion system, to permit temporary disconnection and subsequent re-connection of a medication infusion pump relative to a patient without requiring removal of a transcutaneous infusion cannula. The coupling is mounted in-line with a length of infusion tubing and includes a female component with a needle recessed therein and adapted for slide-fit connection with a male component having a self-sealing septum. Radial tabs on the male component slide freely into longitudinally open slots formed in the female component, whereupon the male component is rotatable to displace the tabs with interference fit past undercut cam surfaces into alignment with radially open ports formed in the female component. When connected, the male and female components are effectively locked against longitudinal separation. However, the male and female components can be separated safely and easily, and without applying substantial longitudinal forces, by rotating the male component to displace the tabs back to alignment with the longitudinally open slots in the female component.

17 Claims, 5 Drawing Sheets

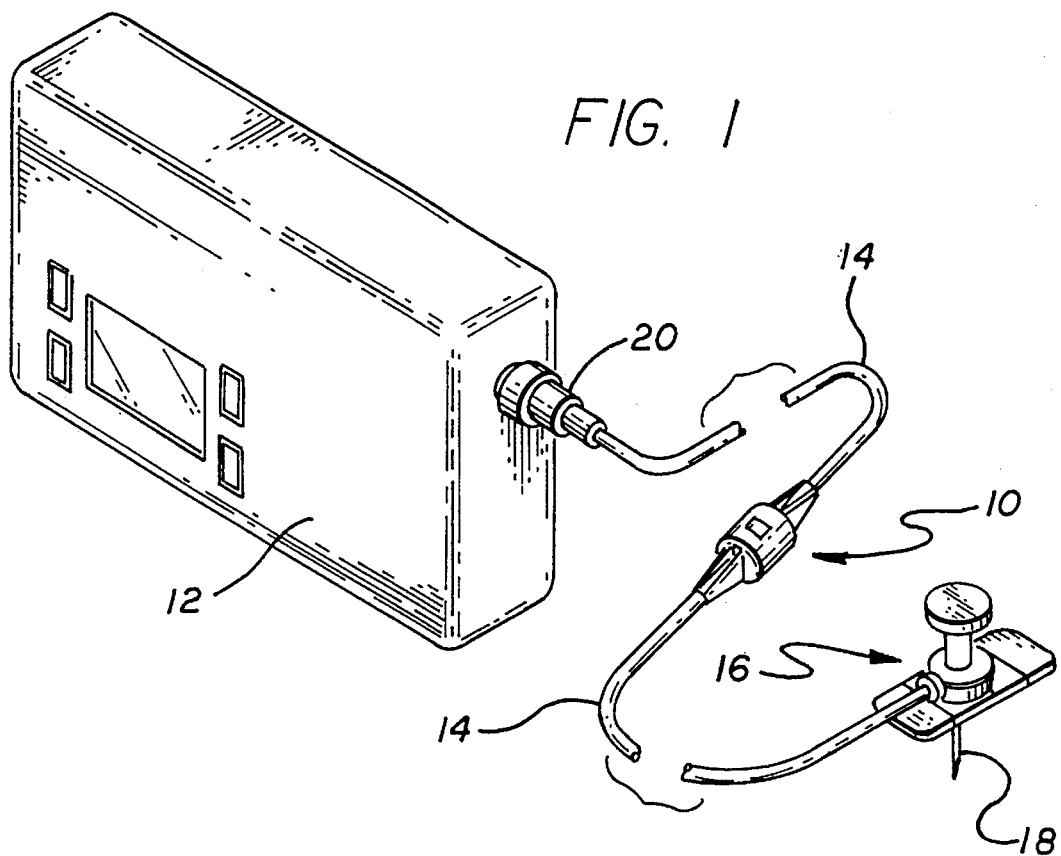
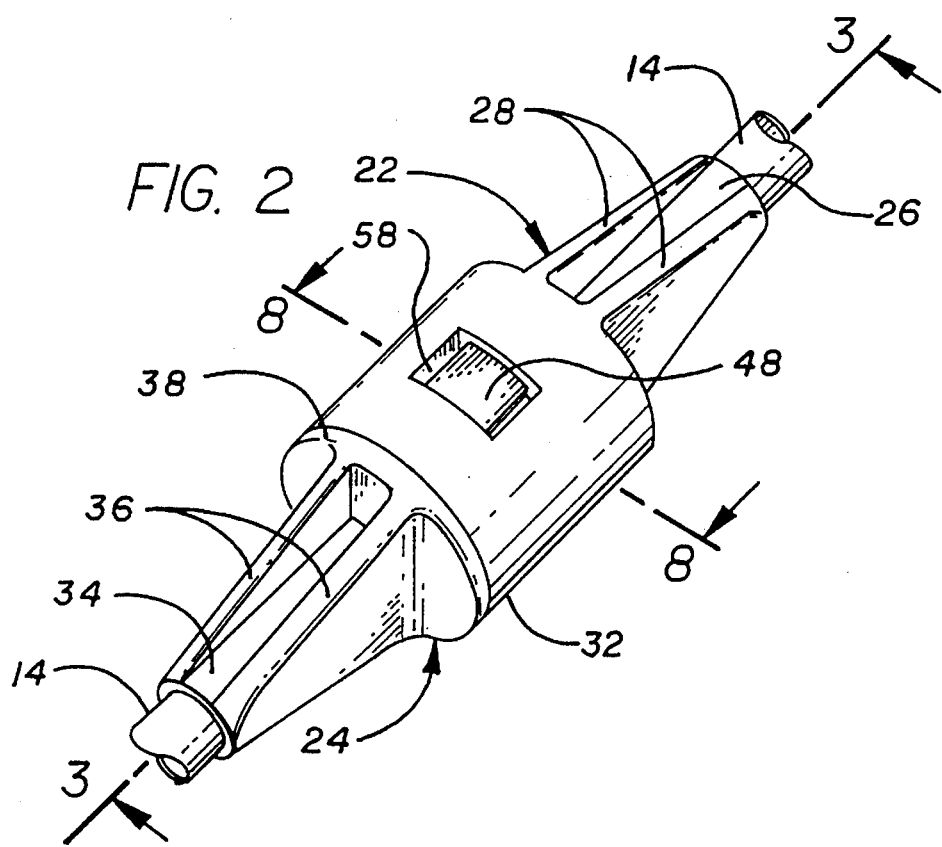

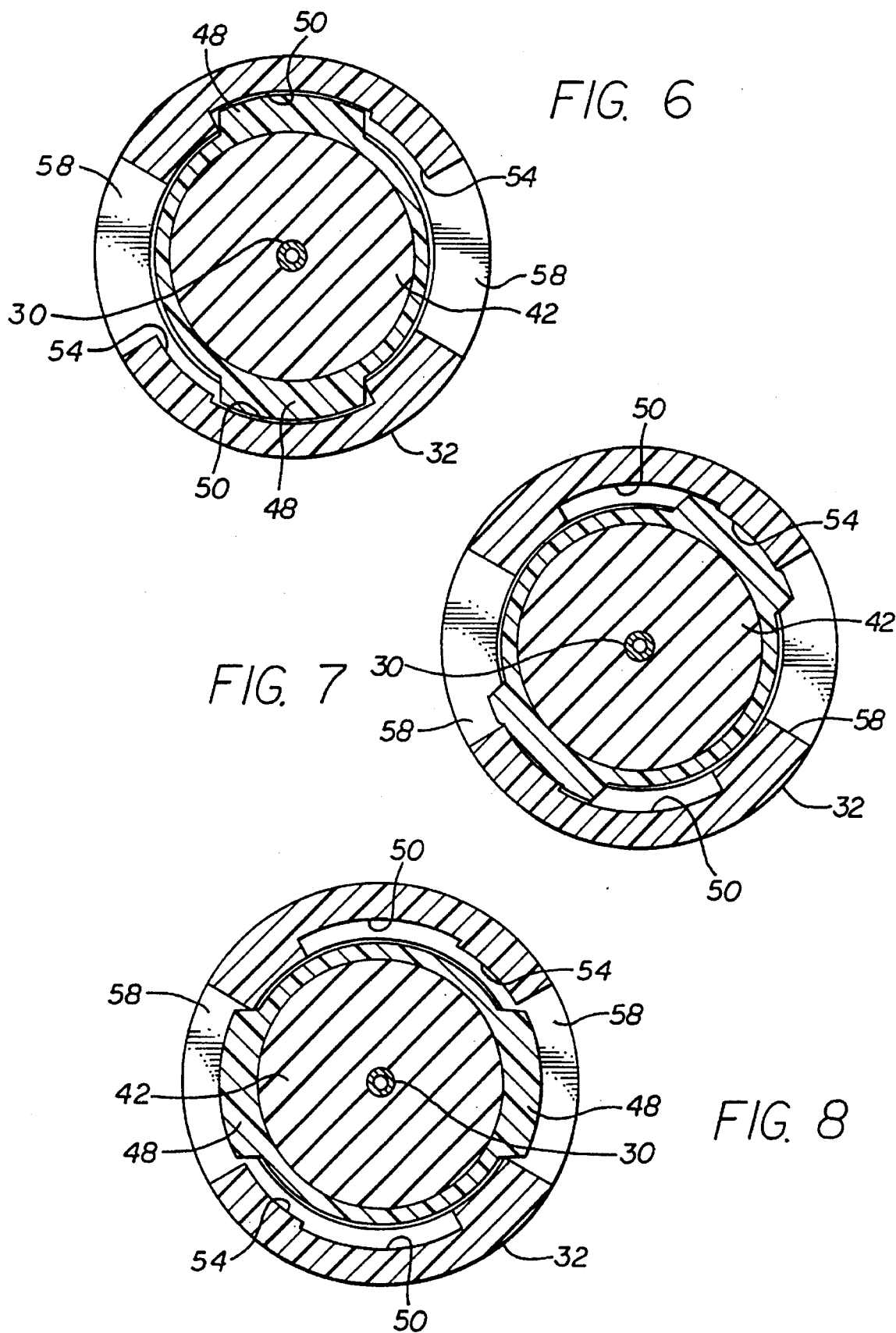

QUICK-CONNECT COUPLING FOR A MEDICATION INFUSION SYSTEM

BACKGROUND OF THE INVENTION

This invention relates generally to improvements in medical fluid infusion systems and devices for delivering a selected infusion fluid to a patient. More particularly, this invention relates to an improved and easily manipulated quick-connect coupling mounted in-line with a length of infusion tubing to permit temporary disconnection and subsequent re-connection of an infusion fluid source relative to a patient, without requiring removal of a transcutaneous infusion cannula from the patient.

Medical fluid infusion systems are generally known in the art for use in delivering a selected infusion fluid to a patient. In one common form, a relatively compact infusion pump is adapted to receive a syringe or the like carrying a selected medication for administration to a patient through a length of infusion tubing and a transcutaneously placed infusion cannula. The infusion pump includes a small drive motor for controlled advancement of a syringe piston plunger to administer the medication to the patient. Programmable control means are normally provided for operating the drive motor continuously or at periodic intervals to obtain a closely controlled and accurate delivery of medication over an extended time period. Such infusion pumps are utilized to administer insulin and other medications, with exemplary pumps being marketed by MiniMed Technologies, of Sylmar, California under model designations 504 and 506. See also U.S. Pat. Nos. 4,562,751; 4,678,408; and 4,685,903 pertaining to medication infusion pumps, and U.S. Pat. Nos. 4,755,173; 5,176,662; and 5,257,980 pertaining to infusion sets having a transcutaneous infusion cannula.

Medication infusion pumps and related infusion sets of the general type described above provide significant advantages and benefits with respect to accurate delivery of the medication over an extended period of time. The infusion pump is often designed to be extremely compact and thus may be adapted to be carried by the patient. As a result, the medication can be administered with precision and in an automated manner, without significant restriction on the patient's mobility or life-style.

Despite the many advantages and benefits of compact medication infusion pumps, the patient is required to exercise at least some degree of caution in order to protect against accidental damage to the pump and/or accidental removal of the transcutaneous infusion cannula. In this regard, to safeguard the pump, it may be necessary or desirable to temporarily disconnect the pump from the patient whenever the patient is involved in an activity which might subject the pump to potential damage. Such short-term activities may include, for example, bathing or showering, swimming, or similar activities which might expose the pump to water damage. Similarly, disconnection of the pump may be desirable when the patient participates in certain athletic activities which might otherwise expose the pump to potential impact damage. It is, of course, desirable to promptly re-connect the medication infusion pump to the patient when such activity is concluded.

In the past, temporary pump disconnection from the patient has typically been accomplished by removing the infusion cannula from the patient. Unfortunately, this technique requires subsequent re-placement of the cannula with an insertion needle. Such re-placement of the cannula with an insertion needle must be done under sterile conditions and involves repeated and undesirable needle sticks. Alternative techniques have utilized quick-connect couplings adapted for in-line mounting along the infusion tubing. However, prior quick-connect couplings designed for periodic separation have typically encountered problems with accidental separation of the coupling components, or have otherwise required the application of substantial manual force to separate the coupling components. In the latter case, when substantial force is applied to pull apart the coupling components, there is a significant risk of inadvertently removing the infusion cannula from the patient. In another alternative, temporary pump disconnection can be achieved by temporary removal of the medication containing syringe from the pump, but this approach requires the patient to handle the syringe at the now-unsupported end of the infusion tubing and also presents problems in re-installation of the syringe into the pump.

The present invention is directed to an improved yet relatively simple and safe quick-connect coupling designed to permit temporary disconnection and subsequent re-connection of a medication infusion pump relative to a patient, without requiring high longitudinal separation forces to thereby protect against inadvertent removal of a transcutaneous infusion cannula from a patient.

SUMMARY OF THE INVENTION

In accordance with the invention, a quick-connect coupling is provided for use in a medication infusion system, particularly of the type having a compact medication infusion pump for programmed delivery of a selected medication through a length of infusion tubing and a transcutaneous infusion cannula to a patient. The quick-connect coupling is mounted in-line along the infusion tubing and includes a female component and male component adapted for slide-fit connection and separation without requiring the application of substantial longitudinal forces. When connected, the male and female components of the quick-connect coupling are effectively locked against accidental longitudinal separation.

In the preferred form of the invention, the female component of the quick-connect coupling is mounted at the end of a first segment of the infusion tubing connected to the medication infusion pump. The female component has a generally cylindrical, open-ended shape with a connector needle mounted therein in flow communication with the tubing segment. Importantly, the connector needle is recessed within the female component to prevent accidental contact therewith and resultant accidental needle sticks.

The male component is mounted at the end of a second segment of infusion tubing connected to the infusion cannula on the patient. The male component includes a generally tubular nose adapted for slide-fit connection with the female component. A self-sealing septum is carried by the male component and is pierced by the connector needle upon slide-fit interconnection of the male and female components.

The male component has at least one and preferably a pair of radially raised tabs for slide-fit reception into a corresponding number of longitudinally open entry slots formed within the female component. The tabs and slots are sized to permit slide-fit connection and disconnection of the male and female components in the longitudinal direction, in response to minimal longitudinal force applied thereto. Thus, the male and female components can be connected and disconnected without jerking which could otherwise damage the infusion tubing or result in inadvertent removal of the infusion cannula from the patient.

The male and female components include axial stops which engage upon full reception of the male component into the female component. The male component is then rotatable within the female component to displace the tabs with an interference fit past undercut cam surfaces to position the tabs with a snap-fit action within radially open ports formed in the female component. In this position, the tabs are effectively locked within these ports to prevent inadvertent longitudinal separation of the coupling components. However, when temporary disconnection is desired, the male component can be back-rotated to displace the tabs past the undercut cam surfaces into re-alignment with the open entry slots, whereupon the male and female components can be longitudinally separated with minimal longitudinal force.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view illustrating a medication infusion system including a quick-connect coupling embodying the novel features of the invention;

FIG. 2 is an enlarged fragmented perspective view illustrating the quick-connect coupling of FIG. 1;

FIG. 6 is a transverse sectional view illustrating initial slide-fit connection of the coupling components;

FIG. 7 is a transverse sectional view similar to FIG. 6, but illustrating rotatable displacement of the male component within the female component toward a locked position; and FIG. 8 is a transverse sectional view similar to FIGS. 6 and 7, taken generally on the line 8—8 of FIG. 2, and illustrating the coupling components in the locked position.

DETAILED DESCRIPTION OF THE PREFERRED EMBODIMENT

Figure 3:
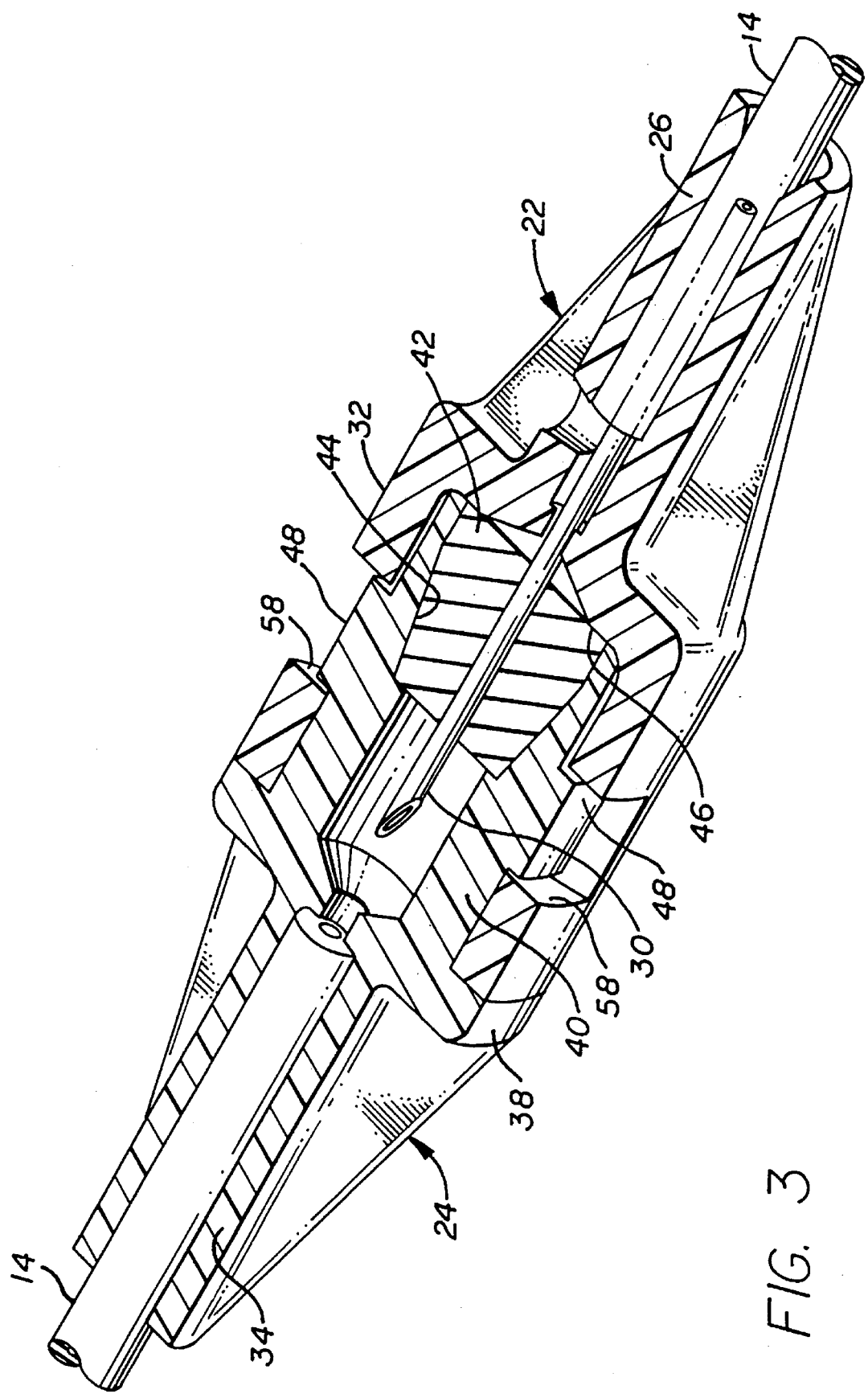
FIG. 3 is a longitudinal sectional view taken generally on the line 3—3 of FIG. 2.

As shown in the exemplary drawings, an improved quick-connect coupling referred to generally by the reference numeral 10 is provided for use in a medication fluid infusion system having a medication infusion pump 12 for delivering a selected medication through infusion tubing 14 and an infusion set 16 to a patient (not shown). The quick-connect coupling 10 permits temporary disconnection and subsequent re-connection of the pump 12 with respect to a patient, without requiring removal of a transcutaneous infusion cannula 18 from the patient.

The medication infusion pump 12 (FIG. 1) has an overall construction and operation which is generally known in the art. More specifically, the infusion pump 12 is provided in the form of a relatively compact unit adapted to receive and support a syringe or the like charged with a selected medication, such as insulin, to be administered to the patient. The pump 12 is appropriately manipulated and/or programmed to administer the medication to the patient in a programmed manner over a selected and potentially extended time period. As shown in FIG. 1, the medication is delivered from the pump via a luer fitting 20 and the infusion tubing 14 to the infusion administration set 16 which includes the cannula 18. Medication infusion pumps of this general type are described in U.S. Pat. Nos. 4,562,751; 4,678,408; and 4,685,903 which are incorporated by reference herein. Such infusion pumps are available from MiniMed Technologies of Sylmar, California under model designations 504 and 506. Infusion administration sets of the type depicted in FIG. 1 are described in U.S. Pat. Nos. 4,755,173; 5,176,662; and 5,257,980, which are also incorporated by reference herein.

The quick-connect coupling 10 of the present invention accommodates safe and easy disconnection of the pump 12 from a patient, as may be required on a temporary basis when the patient is involved in an activity which might otherwise result in damage to the pump. Such activities may include, for example, bathing, showering or swimming, wherein it is desirable to protect the pump against contact with water. Other activities may include, for example, various sports activities wherein it is desirable to protect the pump against impact-caused damage. Importantly, the coupling 10 permits the pump to be disconnected without applying large longitudinal forces to the infusion tubing 14, whereby there is little or no risk of inadvertently dislodging the infusion cannula 18 from the patient. Similarly, the coupling 10 accommodates quick and easy re-connection, again without requiring the application of large longitudinal forces to the tubing or coupling components. When connected, the coupling 10 is effectively locked against inadvertent longitudinal separation.

The quick-connect coupling 10 is shown in more detail in FIGS. 2–5, and generally comprises a female component 22 adapted for slide-fit interconnection with a male component 24. In general terms, these coupling components 22 and 24 are slidably interconnected with minimal longitudinal force to establish a fluid connection between the pump 12 and the infusion cannula 18. When this fluid connection is established, the male component 24 is rotated within the female component 22 to achieve a locked condition wherein the components are effectively locked against axial separation.

Figure 4:
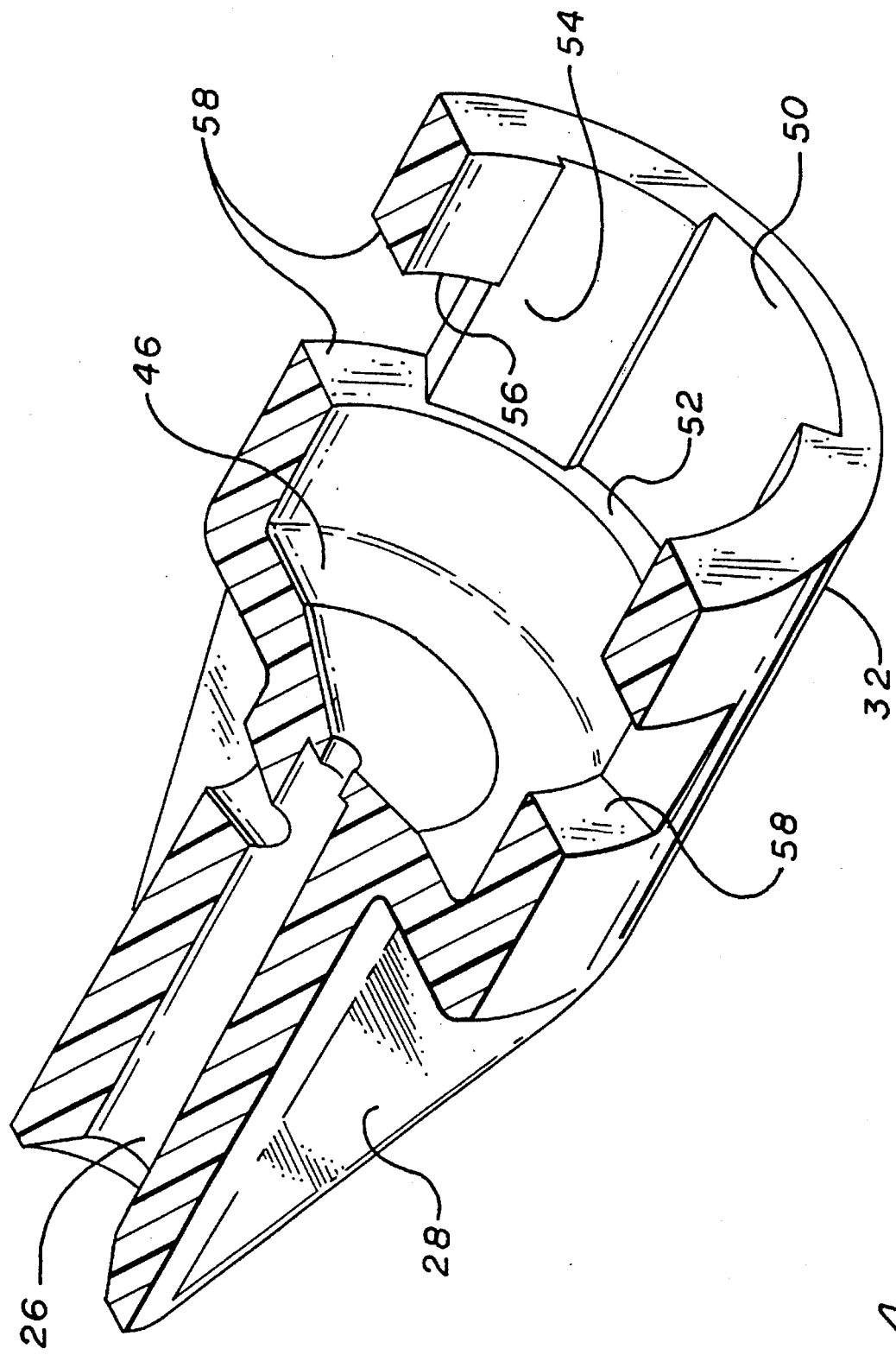
FIG. 4 is a longitudinal sectional view similar to FIG. 3, but illustrating a female component of the quick-connect coupling with a male-component of the coupling removed therefrom.

As shown best in FIGS. 3 and 4, the female component 22 includes a tubular ferrule 26 for receiving the end of the infusion tubing segment connected to the pump 12. This tubing segment is desirably secured within the ferrule 26 as by means of a suitable adhesive or the like. Flat-sided ribs 28 are formed on the exterior of the ferrule 26 to facilitate manual grasping and manipulation of the female component 22 during connection and disconnection procedures, as will be described.

A connector needle 30 has a proximal end seated within the infusion tubing segment, within the ferrule 26 of the female component 22. As shown best in FIGS. 3 and 4, the connector needle 30 projects outwardly from the ferrule to extend coaxially within an enlarged cylindrical fitting 32 of the female component 22. The pointed distal end of the connector needle 30 terminates at least slightly short of the open end of the fitting 32, whereby the connector needle 30 is recessed within the female component 22 and thereby shielded against inadvertent fingertip contact and undesirable needle sticks associated therewith.

The male component 24 of the coupling 10 also includes a ferrule 34 connected in a similar manner to the end of an infusion tubing segment connected to the infusion set 16 (FIG. 1). The male ferrule 34 also includes external ribs 36 of a flat-sided shape to facilitate manual grasping and manipulation of the male component. The ferrule 34 and ribs 36 are joined at one end to a circular stop plate 38, and a cylindrical nose 40 protrudes axially from the stop plate 38 for slide-fit reception into the open-ended fitting 32 of the female component 22. A self-sealing resilient septum 42 of a suitable elastomer material is securely mounted mechanically within a matingly shaped counterbore 44 of the nose 40, by means of a swaged rib (not shown) or other suitable mounting means.

Figure 5:
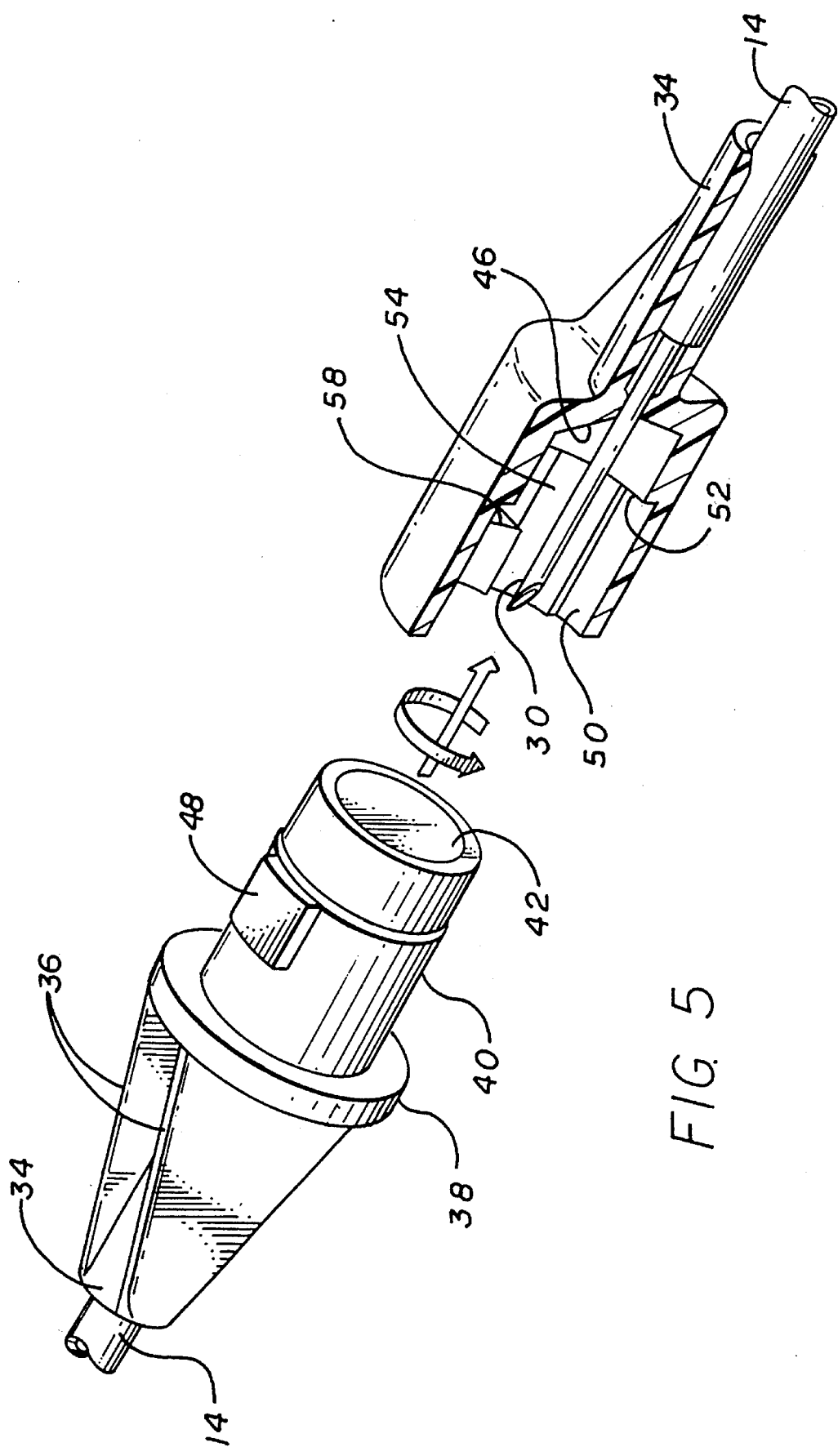
FIG. 5 is an exploded perspective view illustrating slide-fit connection of the male and female components of the quick-connect coupling, with the female component being shown in longitudinal section.

As shown in FIGS. 3 and 5, the male and female components 24, 22 of the quick-connect coupling 10 are slidably connected by slide-fit reception of the male nose 40 into the female fitting 32. This slide-fit connection is accompanied by the connector needle 30 piercing the septum 42 to establish a fluid flow path through the coupling 10, between the infusion tubing segments associated therewith. The coupling components are fully engaged in the longitudinal direction when the distal end of the male nose 40 contacts an annular base wall 46 of the female fitting 32, and/or when the distal end of the fitting 32 axially abuts the stop plate 38 on the male component 24.

Longitudinal slide-fit connection of the coupling components occurs in response to relatively minimum longitudinal forces. In this regard, the male component 24 includes one and preferably a pair of symmetrically oriented tabs 48 which project radially outwardly from the nose 40. These tabs are located at axial positions spaced from the stop plate 38. The radial dimensions of the tabs 48 are chosen for substantially free sliding reception into matingly shaped and longitudinally open entry slots 50 formed within the cylindrical fitting 32 of the female component 22. When the components are fully engaged, the longitudinal leading edges of the tabs 48 are positioned adjacent an annular stop shoulder 52 formed within the female fitting 32.

When the components 22, 24 are fully engaged in the longitudinal direction, the male component 24 can be rotated within the female component toward a locked position. More specifically, as shown best in FIGS. 4 and 6–8, such rotation displaces the tabs 48 in a rotational direction for interference fit engagement with undercut cam surfaces 54 formed within the female fitting 32. The undercut geometry of these cam surfaces 54 thus provides a stop shoulder 56 at the trailing edges of the tabs 48, wherein these stop shoulders 56 positively prevent longitudinal separation of the coupling components when in the locked position.

Continued rotation of the male component 24 within the female component 22 displaces the tabs 48 past the cam surfaces 54 and into alignment with radially open lock ports 58 formed in the female fitting 32. The tabs 48 enter the lock ports 58 with a snap-action. Thus, the tabs 48 are effectively locked within the ports 58, to positively prevent longitudinal separation of the coupling components. This connection is highly resistant to accidental longitudinal separation of the coupling components.

When coupling disconnection is desired, the male component 24 must be back-rotated within the female component 22, to move the tabs 48 past the cam surfaces 54 into re-alignment with the entry slots 50. Such back-rotation of the coupling components can be performed relatively easily, but essentially requires an affirmative intent by the patient to disconnect the coupling. It is important to note that this unlocking back-rotation of the male component does not require the application of any longitudinal forces to the coupling or the related infusion tubing. When the tabs are re-aligned with the entry slots 50, the male and female components can be separated easily and with minimal longitudinal force. Accordingly, the coupling can be disconnected with little or no risk of jerking motions which could otherwise pull the infusion cannula 18 from the patient.

The quick-connect coupling 10 of the present invention thus provides for safe and easy disconnection and subsequent re-connection of an infusion fluid source, such as a medication infusion pump from a patient. Substantial longitudinal connection and disconnection forces are not required. However, when the coupling is fully connected, the coupling components are effectively locked against longitudinal separation to correspondingly safeguard against inadvertent disconnection.

A variety of further modifications and improvements to the quick-connect coupling of the present invention will be apparent to those skilled in the art. Accordingly, no limitation on the invention is intended by way of the foregoing description and accompanying drawings, except as set forth in the appended claims.

What is claimed is:

1. A quick-connect coupling for a medication infusion system, comprising:

a female component having an open-ended, generally cylindrical fitting; and a male component having a nose for slide-fit reception into said cylindrical fitting of said female component;

said male component having a radially raised tab on said nose with a size and shape for substantially free slide-fit reception into a longitudinally open entry slot formed within said cylindrical fitting of said female component;

said male component being rotatable with said nose received within said fitting to displace said tab substantially with an interference fit past an undercut cam surface formed within said fitting and into seated alignment with a radially open lock port formed in said fitting, whereby said male and female components are effectively locked against longitudinal separation.

2. The quick-connect coupling of claim 1 wherein one of said male and female components includes a connection needle, and the other of said male and female components includes a self-sealing septum positioned to be pierced by said connector needle when said nose is slide-fitted into said fitting.

3. The quick-connect coupling of claim 2 wherein said connector needle is mounted on said female component with a pointed end of said needle recessed within said fitting.

4. The quick-connect coupling of claim 1 wherein each of said male and female components includes a ferrule portion for connection to a segment of infusion tubing.

5. The quick-connect coupling of claim 4 wherein said ferrule portions of said male and female components each include flat-sided ribs.

6. The quick-connect coupling of claim 1 wherein said male and female components further include stop means for stopping slide-fit insertion of said nose into said fitting at a position with said tab aligned axially with said undercut cam surface.

7. The quick-connect coupling of claim 1 wherein said tab is sized for snap-fit reception into said lock port.

8. A quick-connect coupling for a medication infusion system, comprising:

a female component defining an open-ended fitting; and a male component defining a nose for slide-fit reception into said fitting;

said male component having at least two radially raised tabs on said nose for substantially free slide-fit reception within longitudinally open entry slots formed within said fitting, when said nose is slidably received into said fitting;

said tabs on said male components being axially aligned with cam surfaces formed within said fitting when said nose is fully received into said fitting, whereupon said male component is rotatable relative to said female component to displace said tabs past said cam surfaces for reception into lock ports formed in said fitting to lock said male and female components against longitudinal separation.

9. The quick-connect coupling of claim 8 wherein said tabs are sized for snap-fit reception into said lock ports.

10. The quick-connect coupling of claim 8 wherein one of said male and female components includes a connection needle, and the other of said male and female components includes a self-sealing septum positioned to be pierced by said connector needle when said nose is slide-fitted into said fitting.

11. The quick-connect coupling of claim 10 wherein said connector needle is mounted on said female component with a pointed end of said needle recessed within said fitting.

12. The quick-connect coupling of claim 8 wherein each of said male and female components includes a ferrule portion for connection to a segment of infusion tubing.

13. The quick-connect coupling of claim 12 wherein said ferrule portions of said male and female components each include flat-sided ribs.

14. The quick-connect coupling of claim 8 Wherein said male and female components further include stop means for stopping slide-fit reception of said nose into said fitting when said tabs are axially aligned with said cam surfaces.

15. The quick-connect coupling of claim 8 wherein said cam surfaces are undercut within said fitting.

16. the quick-connect coupling of claim 8 wherein said male component is back-rotatable within said female component to displace said tabs from said lock ports and past said cam surfaces to alignment with said entry slots, said male and female components thereupon being longitudinally separable with minimal force.

17. A medication infusion system, comprising:

a length of infusion tubing:

an infusion set at one end of said tubing for transcutaneous delivery of an infusion fluid to a patient;

an infusion fluid source at an opposite end of said infusion tubing for delivering a selected infusion fluid to the patient; and a quick-connect coupling mounted in-line along the length of the infusion tubing, said coupling including a female component defining an open-ended fitting with a connection needle at a shielded position therein, and a male component defining a nose with a self-sealing septum and adapted for slide-fit reception into said fitting whereby said septum is pierced by said needle;

said male component having a radially raised tab on said nose with a size and shape for substantially free slide-fit reception into a longitudinally open entry slot formed within said cylindrical fitting of said female component;

said male component being rotatable with said nose received within said fitting to displace said tab substantially with an interference fit past an undercut cam surface formed within said fitting and into seated alignment with a radially open lock port formed in said fitting, whereby said male and female components are effectively locked against longitudinal separation.

* * * * *